United States Patent [19]

Steck et al.

[11] Patent Number: 5,077,438

[45] Date of Patent: Dec. 31, 1991

[54] PROCESS FOR THE PREPARATION OF ACROLEIN

[75] Inventors: Werner Steck, Ludwigshafen; Matthias Schwarzmann; Kurt Weinacht, both of Limburgerhof; Franz Merger, Frankenthal, all of Fed. Rep. of Germany

[73] Assignee: BASF Aktiengesellschaft, Ludwigshafen, Fed. Rep. of Germany

[21] Appl. No.: 655,075

[22] Filed: Feb. 14, 1991

[30] Foreign Application Priority Data

Feb. 17, 1990 [DE] Fed. Rep. of Germany ....... 4005163

[51] Int. Cl.$^5$ ............................................. C07C 45/51
[52] U.S. Cl. .................................................. 568/450
[58] Field of Search ............................... 568/450, 485

[56] References Cited

U.S. PATENT DOCUMENTS 2,853,520 9/1958 Newman .............................. 568/450
4,749,814 6/1988 Chabardes .......................... 568/450
4,996,365 2/1991 Lauterbach et al. ............... 568/450

OTHER PUBLICATIONS

Ullmann's Encyclopedia of Industrial Chemistry, vol. A1, (1985) pp. 149 to 160.

Primary Examiner—Mary C. Lee
Assistant Examiner—Jessica Nguyen
Attorney, Agent, or Firm—John H. Shurtleff

[57] ABSTRACT

A method of isomerizing propargyl alcohol to acrolein, wherein propargyl alcohol is rearranged in the gas phase at a temperature of from 300° to 550° C. and a pressure of from 0.01 to 50 bar and in contact with a heterogeneous catalyst containing alkaline-reacting metal ions, and the use of propargyl alcohol as a depot substance for the liberation of acrolein.

7 Claims, No Drawings

PROCESS FOR THE PREPARATION OF ACROLEIN

The present invention relates to a process for the preparation of acrolein by hetero-catalyzed isomerization of propargyl alcohol in the gas phase using a heterogeneous catalyst which contains alkaline-reacting metal ions.

A number of manufacturing processes for the preparation of acrolein has been described According to Ullmann's *Encyclopedia of Industrial Chemistry, Volume A* 1, (1985), pp. 149 to 160, acrolein can be synthesized by oxidizing propene or by condensing acetaldehyde and formaldehyde in the gas phase. However, due to the toxicity of acrolein and its tendency to polymerize, it can be kept in storage only for a limited period of time and only with the observance of expensive precautionary measures.

It is thus an object of the present invention to provide a depot substance for acrolein, which can be readily converted to acrolein so as to provide the latter as and where required for participation in chemical reactions.

Accordingly, we have found a novel method of isomerizing propargyl alcohol to acrolein, wherein propargyl alcohol is rearranged in the gas phase at a temperature of from 300° to 550° C. and a pressure of from 0.01 to 50 bar and in contact with a heterogeneous catalyst containing alkaline-reacting metal ions.

Propargyl alcohol (propyn-2-ol-1) is industrially readily obtainable from acetylene and formaldehyde.

Thus one possibility is to liberate acrolein from propargyl alcohol in an in-line reactor preceding the reactor in which the acrolein is required for chemical reaction. Alternatively, propargyl alcohol may be used as such, in situ, as a source of acrolein, for direct reaction with, say, dienes.

The reaction conditions which are suitable for said conversion in the gas phase are a temperature of from 300° to 550° C. and a pressure of from 0.01 to 50 bar, preferably atmospheric pressure, the throughput WHSV being from 0.8 to 8 h$^{-1}$ (the WHSV being calculated in terms of grams of starting mixture per gram of catalyst per hour). The reaction may be carried out batchwise or, preferably, continuously at, say, atmospheric pressure in a fixed bed or fluidized bed with or without continuous catalyst regeneration.

The reaction may be carried out in the presence of an inert gas such as $N_2$, $CO_2$ or a noble gas, or said gas may be passed through the reaction mixture during the reaction. It is preferred to operate continuously in all embodiments. As long as provision is made for an adequate residence time, the reaction may even be carried out under a reduced pressure of from 0.01 to 0.99 bar.

Suitable catalysts for use in the process of the invention are heterogeneous catalysts containing, for example, cations of alkali metals and/or alkaline earth metals.

The isomerization which takes place in the process of the invention is presumably due in part to the well-known alkaline nature of the said cations in the form of their oxides, hydroxides or salts. For example, the following hydroxides: NaOH, KOH, CsOH, Ca(OH)$_2$, Sr(OH)$_2$, and Ba(OH)$_2$, and the following oxides: MgO, CaO, SrO and BaO, have been found to be suitable. These ions, salts, oxides or other compounds may be used in the present process partly in a pure form, say as MgO, and partly in the form of substances incorporated in molecular sieves such as zeolites and phosphates of related structure or in the form of substances deposited on supporting materials. Examples of suitable supporting materials are $Al_2O_3$ and other aluminum oxides, aluminum silicates, magnesium/aluminum silicates and clay minerals, $SiO_2$ and other siliceous supporting materials or precipitated metal phosphates of divalent or trivalent cations such as Ca, Sr, Ba or Al and B.

There are various ways of determining the degree of suitability of a specific catalyst and thus of defining the requisite amount of catalytically effective ions or compounds. One method is to ascertain the pH of an aqueous catalyst suspension by boiling, say, 1 g of the catalyst in 10 g of distilled water for 10 minutes, removing the catalyst by filtration and then measuring the pH of the clear filtrate either after this has cooled down to 22° C. or beforehand with the pH meter set to compensate for the temperature. The pH reading should be at least 8, whilst in the case of highly suitable catalysts it may be 9 or higher.

Another method makes use of a base-catalyzed, intramolecular gas-phase cyclization of acetonyl acetone, a 1,4-diketone, to 3-methylcyclopentenone, as described by R. M. Dessau in Recent Research Report 214 of the International Zeolite Conference, Amsterdam, July 10–14, 1989, pp. 457 to 458, which provides an indication of whether a specific catalyst is suitable or not. If the catalyst has acid-reacting or predominantly acid-reacting properties, cyclization of the diketone will lead to 2,4-methylfuran instead of 3-methylpentenone as in the case of a base-reacting catalyst. Amphoteric catalysts which act both as an acid and as a base may, when used in said reaction, simultaneously produce both of these heterocyclic compounds in varying proportions.

When catalysts which are suitable for the process of the invention are tested at a temperature of 350° C. and a throughput (WHSV) of 4/h, they generally produce a proportion of at least 70% of 3-methylcyclopentenone in addition to 2,5-dimethylfuran. Thus even amphoteric catalysts may be suitable for the process of the invention provided their base-reacting properties predominate.

One method of applying the metal ions to be used in accordance with the present invention to supporting materials is to impregnate the said support with, say, a hydroxide, nitrate, carbonate, oxide or alcoholate of the aforementioned cations in aqueous, alcoholic or ammoniacal solution, for example by drumming the support in said solution in a rotary evaporator. This is usually followed by at least one drying operation and optionally by calcination at a temperature of from, say, 400° to 700° C., by means of which any carbonates, hydroxides, hydrates or nitrates on the impregnated support are converted to alkali metal or alkaline earth metal oxides, which act as bases. Another method of making suitable catalysts is to impregnate the freshly precipitated supporting material, e.g. a phosphate or silica gel, with a solution containing an alkali metal and/or alkaline earth metal. In another embodiment, the said alkali metal or alkaline earth metal ions may be present in the medium in which the supporting material is precipitated.

Other useful catalysts for the process of the invention are zeolitic substances or solids having a related structure. i.e. molecular sieves, these being imparted with their particular catalytic properties by ion exchange, impregnation or other modifying means involving the inclusion of alkali metal ions or alkaline earth metal ions.

Zeolites are divided into various groups according to their structure. The cavities and pores therein vary in size depending on how the elementary structural units are interlaced. Zeolites are therefore classified, inter alia, as A, L, X, or Y types or as pentasils. The chemical composition and structure of, for example, mordenite and faujasite are given in the Atlas of Zeolite Structure Types, W. M. Meier and D. H. Olsen, Butterworth's Edition, 1987.

Zeolites suitable fur use in the process of the invention are for example the pentasil-type zeolites, which have a structural unit comprising a five-membered ring composed of TO4 tetrahedrons, the cation T being for example Si, Al, Ga, B or Fe. The definition of the pentasil-type zeolites is formulated by G. T. Kokotailo and W. M. Meier in Chem. Soc. Spec. Publ. (1980) 33, pp. 133 to 139. These pentasil zeolites are characterized by a pore size which is between that of the type A zeolites and that of type X or type Y zeolites. The manufacture of such pentasil-type zeolites is described, inter alia, in U.S. Pat. No. 3,702,886 (ZSM-5), U.S. Pat. No. 3,709,979 (ZSM-11) and U.S. Pat. No. 4,061,724 (Silicalite ®). Also included in this group are the isotactic pentasil zeolites described in EP-A 34,727 and the iron silicate zeolites described in DE-A 2,755,770.

If the zeolite has been manufactured in such a manner that it is not in the form desired for catalysis but is, for example, in an acidic H-form, it can be converted to the desired form by ion exchange or by doping or impregnating it with alkali metal ions such as Li, Na, K or Cs or alkaline earth metal ions such as Mg, Ca, Sr or Ba. It is assumed that hydroxides or oxides present on or in the catalyst, for example NaOH, KOH, CsOH, MgO, CaO or even Ba(OH)$_2$ or the like, have a significant effect on the properties of the catalyst.

A suitable modifying method to produce catalysts containing alkali metal ions or alkaline earth metal ions consists, for example, in doping the shaped or unshaped zeolite with an appropriate metal salt by ion exchange or impregnation.

Such doping is advantageously carried out by placing a zeolite, for example a shaped zeolite, in a vertical tube and passing an aqueous solution of a hydroxide of one of the aforementioned cations over the zeolite at a temperature of from 20° to 100° C. Such ion exchange may be effected on the zeolite when it is in its hydrogen, ammonium or alkali metal form, for example.

Another method of applying said metal ions to the zeolite is to impregnate the zeolitic material with, say, a hydroxide, carbonate, oxide or alcoholate of one or more of the aforementioned cations in aqueous, alcoholic or ammoniacal solution, for example by drumming the mixture in a rotary evaporator. Both the ion exchange method and the impregnation procedure will be followed by at least one drying operation and optionally by calcination carried out at a temperature of from 400° to 700° C. In this way, any nitrates, carbonates, hydroxides or hydrates present can be converted into the corresponding alkali metal oxides or alkaline earth metal oxides.

Instead of zeolitic molecular sieves, use may be made of aluminum phosphates or silicon aluminophosphates such as can be synthesized under hydrothermal conditions. These crystalline solids exhibit specific cavity and pore structures related to those of the zeolites. The preparation, properties and classification of these solids on the basis of structure and chemical composition are described in detail by R. M. Barrer in Pure and Appl. Chem. No. 10, pp. 1317 to 1322 (1986) and E. M. Flanigen et al. in Pure and Appl. Chem., Vol. 58, No. 10, pp. 1351 to 1358 (1986) or by N. B. Milestone et al. in Stud. Sci. Catal. (1988), 36 (Methane Conversion), pp. 553 to 562.

Acrolein is an important intermediate suitable for the synthesis of methionine, acrylic acid, glutaric aldehyde, pyridines and other significant chemical substances. The most important uses of acrolein as an intermediate are listed in *Ullmann's Encyclopedia of Industrial Chemistry* 1985, Vol. A, pp. 156 and 157.

EXAMPLES

Gas-phase reaction (general reaction conditions relevant to Table 1)

The gas-phase reactions were carried out under isothermal conditions in a tubular reactor (coil, internal diameter 0.6 cm, length 90 cm) in the presence of a fixed catalyst bed. The amount of catalyst in the fixed bed was varied from 1 g to 10 g to give throughputs ranging from 0.8/h to 8/h (WHSV). Propargyl alcohol was pumped into the reactor at a rate of 10 ml/h and was in the vapor phase by the time it reached the fixed catalyst bed. Nitrogen was used as a protective carrier gas at a rate of 10 l/h (STP). The reaction products were condensed in a cold trap and analyzed by gas chromatography.

The results are listed in Table 1 below.

The catalysts used may be in the form of extrudates having a length of from 2 to 4 mm, pellets having a diameter of from 3 to 5 mm or grit having a particle size of from 0.1 to 0.5 mm, which materials may or may not be fluidized.

TABLE 1

Isomerization of propargyl alcohol (C = Comparative Example)

| Ex. No. | Catalyst No. | Amount [g] | T [°C.] | t [h] | Conv. of Propargyl alcohol [%] | Acrolein Yield [%] | Selectivity for acrolein [%] |
|---|---|---|---|---|---|---|---|
| C 1 | 1 | 4 | 350 | 4 | 0.4 | 0.4 | 98.1 |
|  |  |  | 450 | 6 | 3.4 | 2.8 | 80.9 |
| 2 | 2 | 2 | 400 | 2 | 25.1 | 24.5 | 97.4 |
| 3 | 3 | 2 | 350 | 2 | 24.4 | 13.0 | 53.3 |
| 4 | 5 | 2 | 350 | 2 | 6.9 | 6.4 | 92.5 |
| 5 | 4 | 4 | 400 | 2 | 13.6 | 12.2 | 89.6 |
| 6 | 4 | 4 | 450 | 6 | 29.2 | 22.5 | 77.2 |
| 7 | 4(reg.) | 4 | 450 | 6 | 49.3 | 30.8 | 62.5 |
| 8 | 5 | 2 | 400 | 2 | 6.9 | 3.2 | 45.5 |
| 9 | 6 | 2 | 400 | 2 | 6.5 | 5.6 | 85.9 |
|  |  |  |  | 4 | 4.3 | 3.7 | 84.3 |
| 10 | 7 | 2 | 350 | 2 | 11.1 | 6.5 | 58.9 |
| C11 | 8 | 2 | 450 | 2 | 1.7 | 0.4 | 21.8 |
| 12 | 9 | 2 | 450 | 2 | 5.2 | 3.9 | 75.1 |
| C13 | 10 | 4 | 350 | 2 | 1.0 | 1.0 | 98.4 |
|  |  |  | 450 | 4 | 3.1 | 2.5 | 82.2 |

Comparative Examples 1 and 12 show that an acid catalysis is indeed possible to a slight extent at higher temperatures, due to the Broensted centers of the zeolites; but this catalytic effect, which occurs only at very high temperatures, gives a conversion rate which is far below that achieved using the alkaline catalysis proposed by the present invention.

EXAMPLE C14 (COMPARATIVE EXAMPLE)

2-Butyn-1-ol (b.p. 142°–143° C.) was used in place of propargyl alcohol. Catalyst No. 2 was used at a temperature of 400° C. as specified in Example 2. Isomerization of this product to crotonic aldehyde, which is conceivable, did not take place. Only 4% thereof was converted to worthless low-boiling products (GC analysis). Surprisingly, therefore, the reaction proposed by the present invention is specific only to propargyl alcohol.

EXAMPLE 15

Use of propargyl alcohol as a depot substance for acrolein.

Diels-Alder-reaction of propargyl alcohol with dicyclopentadiene ($C_{10}H_{12}$) to form norbornene carboxaldehyde.

Catalyst No. 2 was used as specified in Example 2 except that the temperature was adjusted to only 350° C. A solution of propargyl alcohol and dicyclopentadiene in a molar ratio of 2:1 was pumped into the reactor at a rate of 10 ml/h, where it evaporated. The conversion of propargyl alcohol was 18%. The condensate contained acrolein (12% v/v as determined by GCA) and residues of dicyclopentadiene (2% v/v, GCA) and also 4% v/v of the desired norbornene aldehyde, as shown by gas chromatographic analysis. This Example shows that propargyl alcohol can serve as a depot substance for acrolein and, accordingly, can be used as an in situ source of acrolein.

Catalyst Preparation

Catalyst No. 1 (Comparative catalyst)

A commercial acidic H-ZSM-5 (pentasil-type zeolite) having a molar ratio of $SiO_2$ to $Al_2O_3$ of 57:1 and a crystal size of less than 0.05 μm, as measured with an electron microscope, was used. This material was shaped to extrudates having a length of 2 mm with the aid of a shaping auxiliary. The extrudates were dried at 110° C. for 16 hours and then calcined at 500° C. for 16 hours. In the catalyst test after Dessau, carried out at 350° C., a 100% conversion of acetonyl acetone to 2,3-dimethylfuran (selectivity 95%) was measured. The pH of the catalyst was 3.1.

Catalyst No. 2

10 g of catalyst No. 1 were mixed with 9 ml of a 1N KOH solution and dried at 110° C. The pH was 9.2.

Catalyst No. 3

10 g of catalyst No. 1 were mixed with 25 ml of a 0.5N NaOH solution and dried at 110° C. The pH was 10.8.

Catalyst No. 4

3 g of sodium methylate were dissolved in 50 ml of methanol, and this solution was added to 15 g of catalyst No. 1 which has been placed in a rotary evaporator. The mixture was drummed to dryness and the resulting catalyst powder was dried in a desiccator cabinet for 3 hours at 110° C.

The pH of the powder was found to be 9.2. In the catalyst test after Dessau, carried out at 350° C. a 100% conversion of acetonyl acetone to 3-methylcyclopentenone (selectivity 93%) was measured.

Catalyst No. 4 (reg.)

After the catalyst No. 4 had been used in Example 6, it was regenerated in the fixed bed reactor by passing air through it for 12 hours at a temperature of 500° C. after which it was used in regenerated form in Example 7 (reg.=regenerated).

Catalyst No. 5

30 g of catalyst No. 1 were suspended in 550 ml of water with stirring at 80° C. and 6 g of CsOH were added over 30 minutes. Stirring was continued for 2 hours at 80° C. and the suspension was then filtered. The filter cake was dried at 110°–120° C.

The powder was then calcined for 4 hours at 500° C. Its pH was found to be 10.4. In the catalyst test after Dessau, carried out at 350° C. an 89% conversion of acetonyl acetone to 3-methylcyclopentenone (selectivity 94%) was measured.

Catalyst No. 6

Commercial MgO was used. This material was shaped to extrudates having a length of 2 mm with the aid of a shaping auxiliary, and the extrudates were then dried at 110° C. and calcined for 16 hours at 500° C. In the catalyst test after Dessau, carried out at 350° C., a 99% conversion of acetonyl acetone to 3-methylcyclopentenone (selectivity 92%) was measured. The pH was 11.1.

Catalyst No. 7 (finely crushed marble)

Commercial CaO was used. In the catalyst test after Dessau, carried out at 450° C., a total conversion of 2% of acetonyl acetone to 3-methylcyclopentenone (selectivity 86%) and to 2,5-dimethylfuran (selectivity 14%) was measured. The pH was 12.8.

Catalyst No. 8

Commercial $SiO_2$ (D 11-10) was used, as was also used as support for catalyst No. 9. In the catalyst test after Dessau, carried out at 350° C., a total conversion of 25% of acetonyl acetone to 3-methylcyclopentenone (selectivity 74%) and to 2,5-dimethylfuran (selectivity 21%) was measured. The pH was 7.3.

Catalyst No. 9

30 g of a commercial $SiO_2$ (D 11-10) as used as catalyst No. 8 were impregnated in a rotary evaporator with 100 ml of a 0.5N $Ba(OH)_2$ solution (baryta solution) and the mixture was drummed to dryness. The catalyst was dried at 110° C. and then calcined for 4 hours at 500° C.

In the catalyst test after Dessau, carried out at 350° C. this catalyst No. 9 produced a total conversion of 77% of acetonyl acetone to 3-methylcyclopentenone (selectivity 89%) and to 2,5-dimethylfuran (selectivity 6%). The pH was 9.8.

Comparative Catalyst No. 10 (composed of ZBM-20/17)

A pentasil-type iron silicate zeolite was synthesized at 165° C. from 273 g of sodium waterglass (27.2% of $SiO_2$, 8.5% of $Na_2O$), 124 g of 1,6-diaminohexane, 521 g of water, 20.6 g of 96% sulfuric acid and 16.1 g of iron-(III) sulfate in a stirred autoclave under hydrothermal conditions and autogenous pressure, at 165° C. Following filtration and washing, the crystalline reaction product was dried at 110° C. for 24 hours and calcined for 24 hours at 500° C. This iron silicate zeolite was composed of 88.1% w/w of $SiO_2$, 7.1% w/w of $Fe_2O_3$ and 0.074% w/w of Na. This material was shaped to extrudates having a length of 4 mm with the aid of a shaping auxiliary, which extrudates were then dried at 110° C. for 16 hours and calcined for 24 hours at 500° C. The extrudates were then placed in a vertical tube and subjected to ion exchange with a 20% w/w $NH_4Cl$ solution four times using 15 ml of solution per g of extrudates each time, the temperature being 80° C. The extrudates were then washed until free from chloride, dried at 110° C. for 10 hours and then calcined for 5 hours at 500° C. The Na content was then 0.015% w/w and the pH was 3.2.

We claim:

1. A method of isomerizing propargyl alcohol to acrolein which comprises:
rearranging propargyl alcohol in the gas phase at a temperature of from 300° to 550° C. and under a pressure of from 0.01 to 50 bar while in contact with a heterogeneous catalyst containing cations of at least one metal selected from the group consisting of alkali metals and alkaline earth metals.

2. A method as claimed in claim 1, wherein said heterogeneous catalyst contains cations in which the alkali metal is selected from the group consisting of Li, K, Na, and Cs and in which the alkaline earth metal is selected from the group consisting of Mg, Ca, Sr, and Ba.

3. A method as claimed in claim 1, wherein the heterogeneous catalyst used in a molecular sieve selected from the group consisting of zeolites and aluminum phosphates of related structure, containing said cations.

4. A method as claimed in claim 1, wherein the heterogeneous catalyst is an alkaline earth metal oxide.

5. A method as claimed in claim 2, wherein the heterogeneous catalyst used is a molecular sieve selected from the group consisting of zeolites and aluminum phosphates of related structure, containing said cations.

6. A method as claimed in claim 1, wherein said heterogeneous catalyst comprises a supporting material impregnated with said cations, said supporting material being selected from the group consisting of aluminum oxides, aluminum silicates, magnesium/aluminum silicates, clay minerals, $SiO_2$ and precipitated phosphates of a metal selected from the group consisting of Ca, Sr, Ba, Al and B.

7. A method as claimed in claim 6, wherein the supporting material is $SiO_2$.

* * * * *